(12) United States Patent
Groth et al.

(10) Patent No.: US 8,150,490 B2
(45) Date of Patent: Apr. 3, 2012

(54) APPARATUS AND METHOD FOR DETERMINING AN INJECTION POINT FOR TARGETED DRUG

(75) Inventors: Alexandra Groth, Aachen (DE); Juergen Weese, Aachen (DE); Joerg Bredno, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1124 days.

(21) Appl. No.: 11/815,878

(22) PCT Filed: Feb. 13, 2006

(86) PCT No.: PCT/IB2006/050459
§ 371 (c)(1),
(2), (4) Date: Aug. 9, 2007

(87) PCT Pub. No.: WO2006/085288
PCT Pub. Date: Aug. 17, 2006

(65) Prior Publication Data
US 2008/0194940 A1 Aug. 14, 2008

(30) Foreign Application Priority Data
Feb. 14, 2005 (EP) .................................... 05101047

(51) Int. Cl.
*A61B 6/00* (2006.01)
(52) U.S. Cl. ........................................ 600/407; 600/431
(58) Field of Classification Search .................. 600/407, 600/419, 420, 431, 458; 382/128, 130–132
See application file for complete search history.

(56) References Cited

U.S. PATENT DOCUMENTS

| 5,919,135 | A | 7/1999 | Lemelson |
| 6,728,566 | B1 | 4/2004 | Subramanyan et al. |
| 2002/0065467 | A1 | 5/2002 | Schutt |
| 2003/0114751 | A1 * | 6/2003 | Pedain et al. ................. 600/431 |
| 2003/0211036 | A1 | 11/2003 | Degani et al. |

FOREIGN PATENT DOCUMENTS

| EP | 14794043 | 11/2004 |
| WO | 03096884 | 11/2003 |
| WO | WO 2004/093684 | * 11/2004 |
| WO | 2006082558 | 8/2006 |

OTHER PUBLICATIONS

Schmitt H, et al; "An X-Ray Based Method", IEEE Transactions on Medical Imaging, vol. 21, No. 3, pp. 251-262, 2002, XP011076267.
Shpilfoygel Simon D, et al; "X-Ray Videodensiomertic Methods"Medical Physics, AIP, vol. 27, No. 9, pp. 2008-2023, 2000, XP012011255.
C Kirbas, F Quek; "A Review of Vessel Extraction Techniques", (VISLAB) Wright State University, Dept. of Computer Science and Engineering, 2002, XP002391558.

* cited by examiner

Primary Examiner — Tse Chen
Assistant Examiner — Peter Luong

(57) ABSTRACT

An apparatus determines an injection point for targeted drug delivery into a patient's body by injection of the drug into a vessel feeding a target area including a target. To provide the interventionalist with an objective and quantitative assessment of potential drug injection points instead of letting him rely on his subjective impression from the visual inspection of DSA sequences, a processor (4) includes an identification routine (41) for identification of a vessel tree topology of vessels feeding the target area, a flow determination routine (42) for determining the percentage of drug material delivered to said target after injection into different potential injection points in the vessel tree, a selection routine (43) for selecting as optimal injection point the potential injection point resulting in the highest percentage of drug delivery to the target.

19 Claims, 4 Drawing Sheets

APPARATUS AND METHOD FOR DETERMINING AN INJECTION POINT FOR TARGETED DRUG

Figure 1:
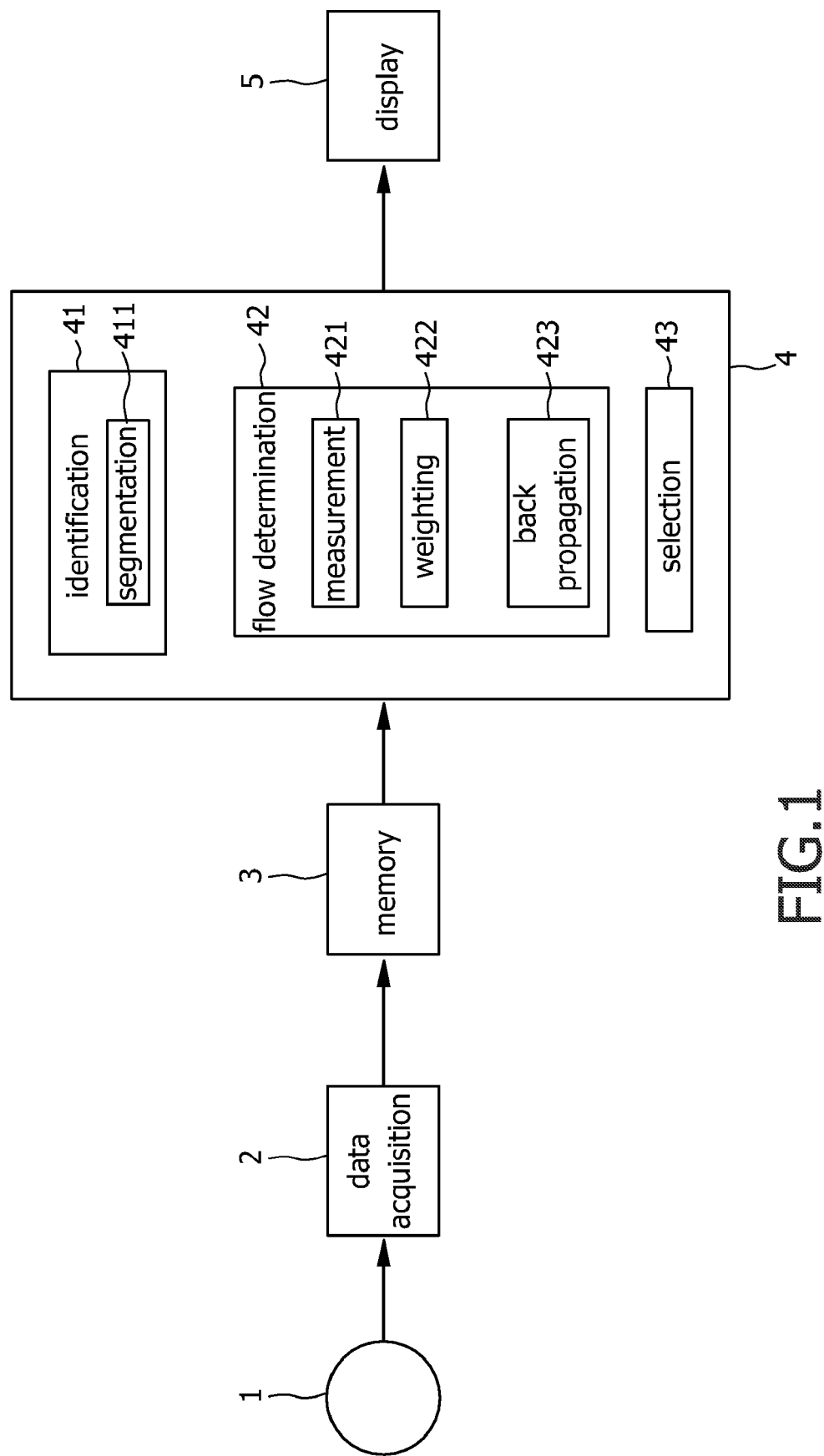

The present invention relates to an apparatus and a corresponding method for determining an injection point for targeted drug delivery into a patient's body by injection of the drug into a vessel feeding a target area including a target. Further, the present invention relates to a computer program for implementing said method on a computer.

Chemoembolization is an effective method of treating unresectable tumors by minimally-invasive means. Under X-ray guidance, a catheter tip is navigated into arteries that supply the tumor. Subsequently, chemoembolic material is injected through the catheter into the tumor. As a result, chemotherapy is directly delivered into the tumor and blood flow to the tumor is blocked.

In order to locate the main feeding arteries of the tumor, contrast agent is injected into candidate vessels and a series of DSA (digital subtraction angiography) images are taken. Following a visual inspection of the spreading of the contrast agent in the vessel tree, the catheter is steered to the optimal injection point. Since this approach is subjective and only based on trial and error, several X-ray acquisitions are required until the seeming optimal point of injection is reached.

If the location of targeted drug delivery is not carefully chosen, the embolus can lodge in the wrong place and deprive normal tissue of its blood supply, which results in the death of healthy cells. Hence, it is crucial to inject the chemoembolic material into arteries feeding mainly the tumor while sparing most of the healthy tissue.

Up to now, no functionality supports the planning of interventions based on transcatheter drug delivery. In addition, the current visual inspection of the contrast agent spreading enables the interventionalist mainly to appraise the present location of contrast agent delivery. Hence, steering the catheter to a better drug injection point becomes a trial-and-error procedure.

U.S. Pat. No. 5,919,135 discloses a method for the determination of the drug dose and for avoiding that the drug leaves the tumor again or that the drug is spread by the venous system. It is suggested to use a location within the image region of the tumor as an injection point. However, no (objective) measurement is used to evaluate this injection point and no better injection point is suggested to the physician. Flow patterns are used to determine the amount of drug that has to be injected and to control the diffusion of such drugs in the venous system. But it is not described how flow patterns are exploited. Blood flow measurement is performed by infusion, but the flow characteristics are not used for the determination of injection points.

It is an object of the present invention to provide an apparatus and a method which provide the interventionalist with an objective and quantitative assessment of potential drug injection points instead of letting him rely on his subjective impression from the visual inspection of DSA sequences. It is a further object that is possible by the apparatus and the method according to the invention to quantify and to visualize both the effectiveness of the tumor treatment and the negative impact on the healthy tissue in close vicinity. In accordance with one aspect, an apparatus includes: identification means for identification of a vessel tree topology of vessels feeding said target area, flow determination means for determining the percentage of drug material delivered to said target after injection into different potential injection points in said vessel tree, selection means for selecting as optimal injection point the potential injection point resulting in the highest percentage of drug delivery to said target.

An objective assessment of potential drug injection points is proposed, which is possible with just a single injection of contrast agent. As a result, information about an optimal injection point or, in a preferred embodiment, a roadmap to the optimal injection point for targeted drug delivery is obtained instantaneously. Due to systematic guidance, the consumption of toxic contrast agent and the duration of X-ray exposure to staff and patients is minimized and the ease-of-use is improved. The invention is based on the idea to assess all potential drug injection points, i.e. segments of the vessel tree, with an objective and quantitative measure in order to provide decision support for a targeted drug delivery and to ensure for systematic guidance to the optimal location. For this purpose, the percentage of injected drug material, e.g. chemoembolic material, delivered to the target, e.g. a tumor, is determined for different potential injection points. By use of the determined percentages the optimal injection point is selected as the injection point having the highest percentage, i.e. if the drug is injected at the optimal injection point the efficiency of drug delivery to the target is maximum and the healthy tissue is harmed to a minimal extent. Furthermore, in a preferred embodiment, the amount of drug effecting healthy tissue is determined in addition. This information can be obtained separately from the percentages of drug delivery to the target, but can also be directly derived from the percentages of drug delivery to the target. When determining the amount of drug effecting healthy tissue, it is taken into account that the damage caused by drug material in healthy tissue depends on the kind of tissue or organ and, of course, on the kind of drug material. Hence, the health risk linked with the potential injection points is evaluated as well. Even if only a minor percentage of the contrast agent is mislead to a wrong tissue region, it might cause devastating damage to essential organs.

The invention is based on the idea to assess all potential drug injection points, i.e. segments of the vessel tree, with an objective and quantitative measure in order to provide decision support for a targeted drug delivery and to ensure for systematic guidance to the optimal location. For this purpose, the percentage of injected drug material, e.g. chemoembolic material, delivered to the target, e.g. a tumor, is determined for different potential injection points. By use of the determined percentages the optimal injection point is selected as the injection point having the highest percentage, i.e. if the drug is injected at the optimal injection point the efficiency of drug delivery to the target is maximum and the healthy tissue is harmed to a minimal extent.

Furthermore, in a preferred embodiment, the amount of drug effecting healthy tissue is determined in addition. This information can be obtained separately from the percentages of drug delivery to the target, but can also be directly derived from the percentages of drug delivery to the target. When determining the amount of drug effecting healthy tissue, it is taken into account that the damage caused by drug material in healthy tissue depends on the kind of tissue or organ and, of course, on the kind of drug material. Hence, the health risk linked with the potential injection points is evaluated as well. Even if only a minor percentage of the contrast agent is mislead to a wrong tissue region, it might cause devastating damage to essential organs.

In a preferred embodiment the volume flow rates in the final segments of the vessel tree are measured in order to determine the amount of drug material entering the target area fed by the vessel tree or the artery feeding said vessel tree. Further, by a back projection of volume flow rates to potential drug injection points, the proportion of drug material which would enter the target can be determined.

According to a further embodiment the volume flow rates are weighted by weighting factors, indicating to what extent the drug harms the tissue located at the end of the respective end segment of the vessel tree. A low weighting factor indicates that the drug has nearly no effect on the tissue whereas a weighting factor close to 1 indicates that the drug destroys the cells. Hence the weighting factors depend on the drug used in the procedure and the tissue that is affected by the drug. The biological impact of a certain drug on certain tissue is written down in tables. The weighting factor for the tissue with the highest impact is equal to one. The others are scaled accordingly.

Preferably, the volume flow rates for each end segment of the vessel tree are weighted with the corresponding weighting factor of the tissue that is fed by this particular artery. Then the way from the end segment to the injection point is determined. The weighted flow rate is assigned to each branch on this way. Thereby it has to be differentiated if the end segment feeds a tumor or healthy tissue. This information is back-propagated, i.e. assigned to each upstream branch, as well.

According to further preferred embodiments of the invention the target itself, e.g. the tumor, or the complete target area, i.e. the area around the target including the target itself and surrounding tissue, is segmented. In the latter case, all compartments of the target area fed by an end segment of the vessel tree are determined for each end segment. For instance, for the liver the number and the principal location of such different segments are well known.

The target is preferably identified through user interaction, e.g. by a mouse click on the tumor. However, generally automatic identification of the target, e.g. by any texture analysis, is possible as well. But since the identification of the target is very easy for the physician and a mouse click or drag around a larger area is an easy procedure, a manual selection is preferred.

As a result the location of the optimal injection point is obtained. This location can be displayed in a display of the vessel tree. Further, the percentages of drug delivery for different segments of said vessel tree or the respective results of the evaluation criterion can be displayed.

Figure 2:
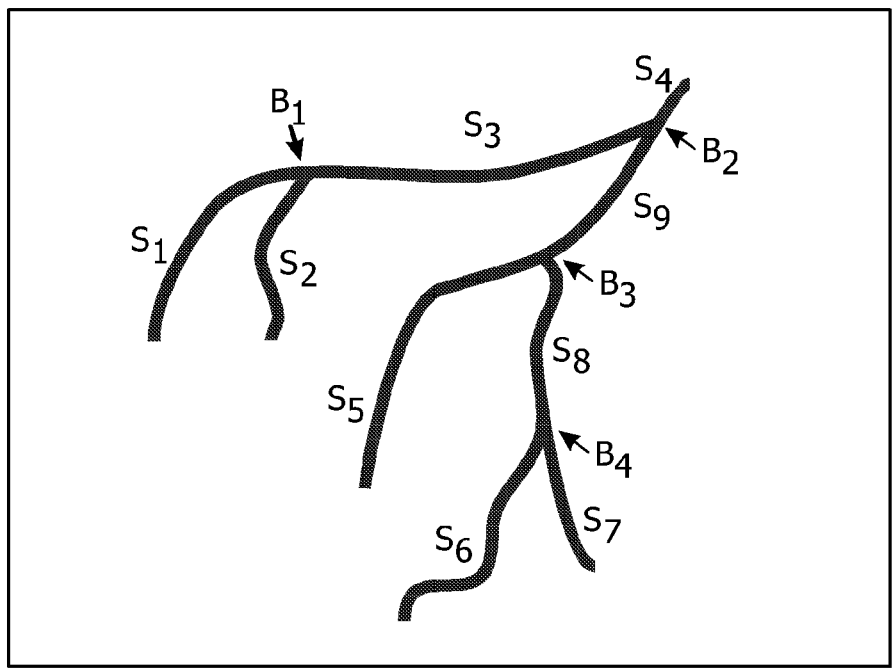
Figure 3:
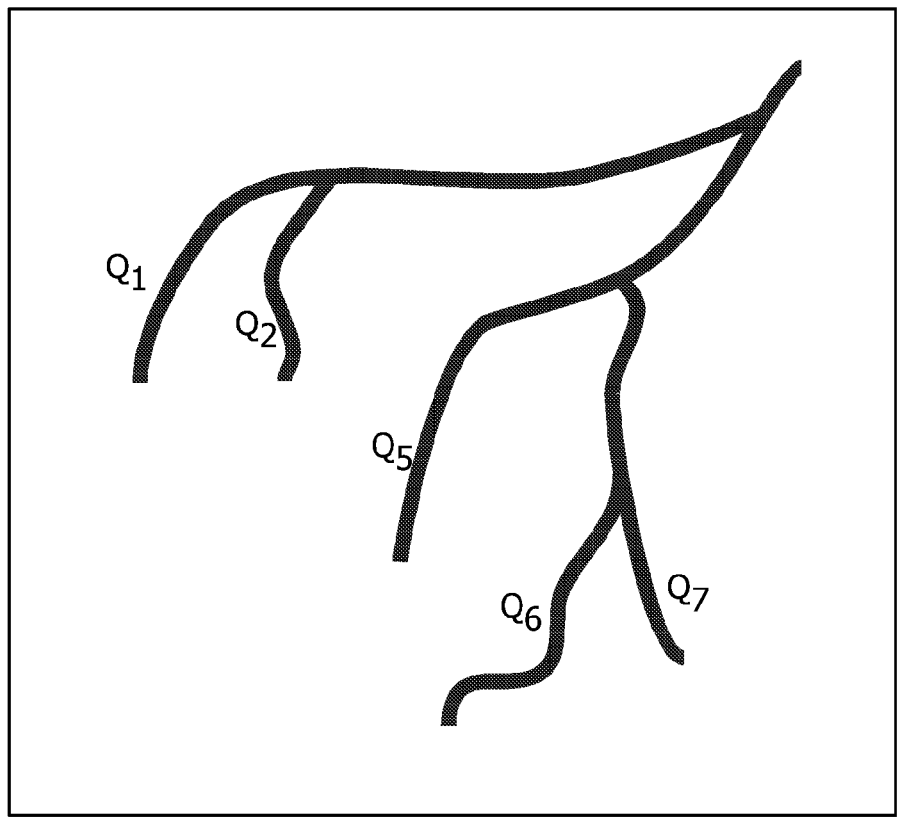
Figure 4:
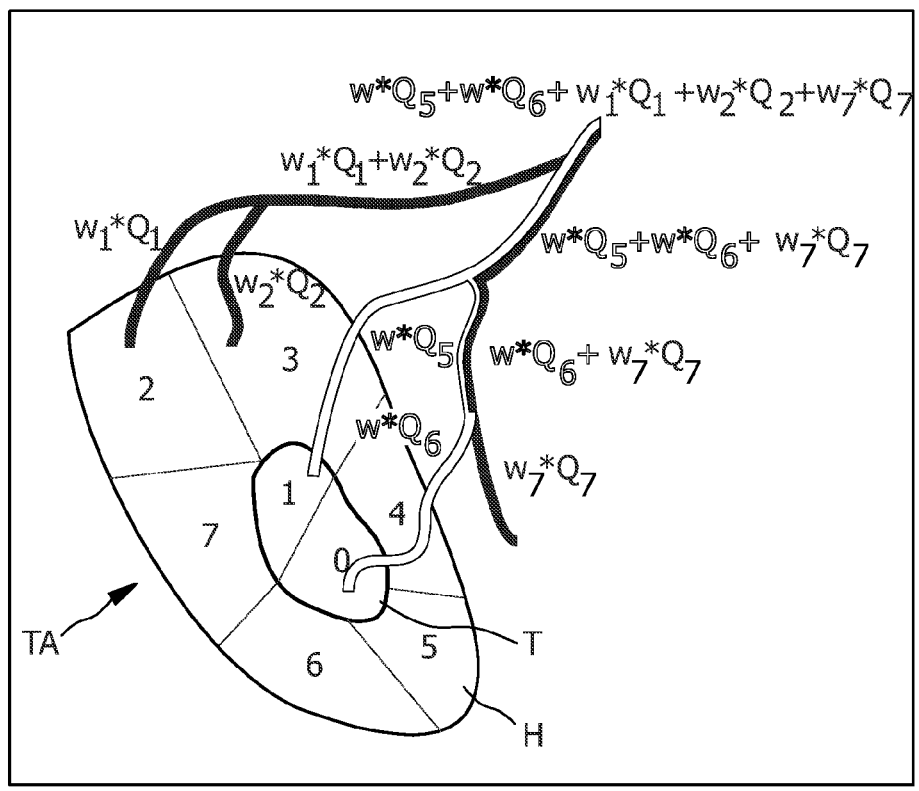
Figure 5:
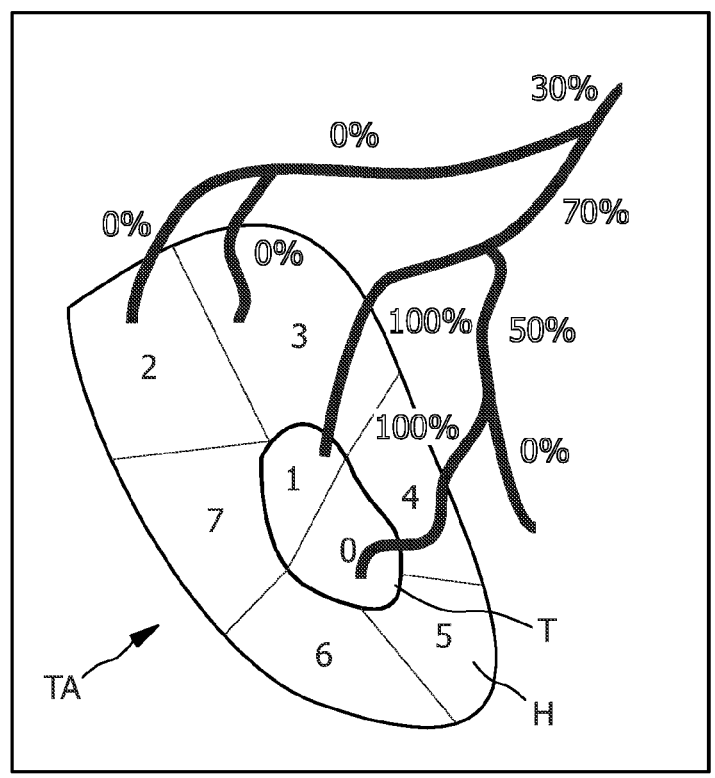
Figure 6:
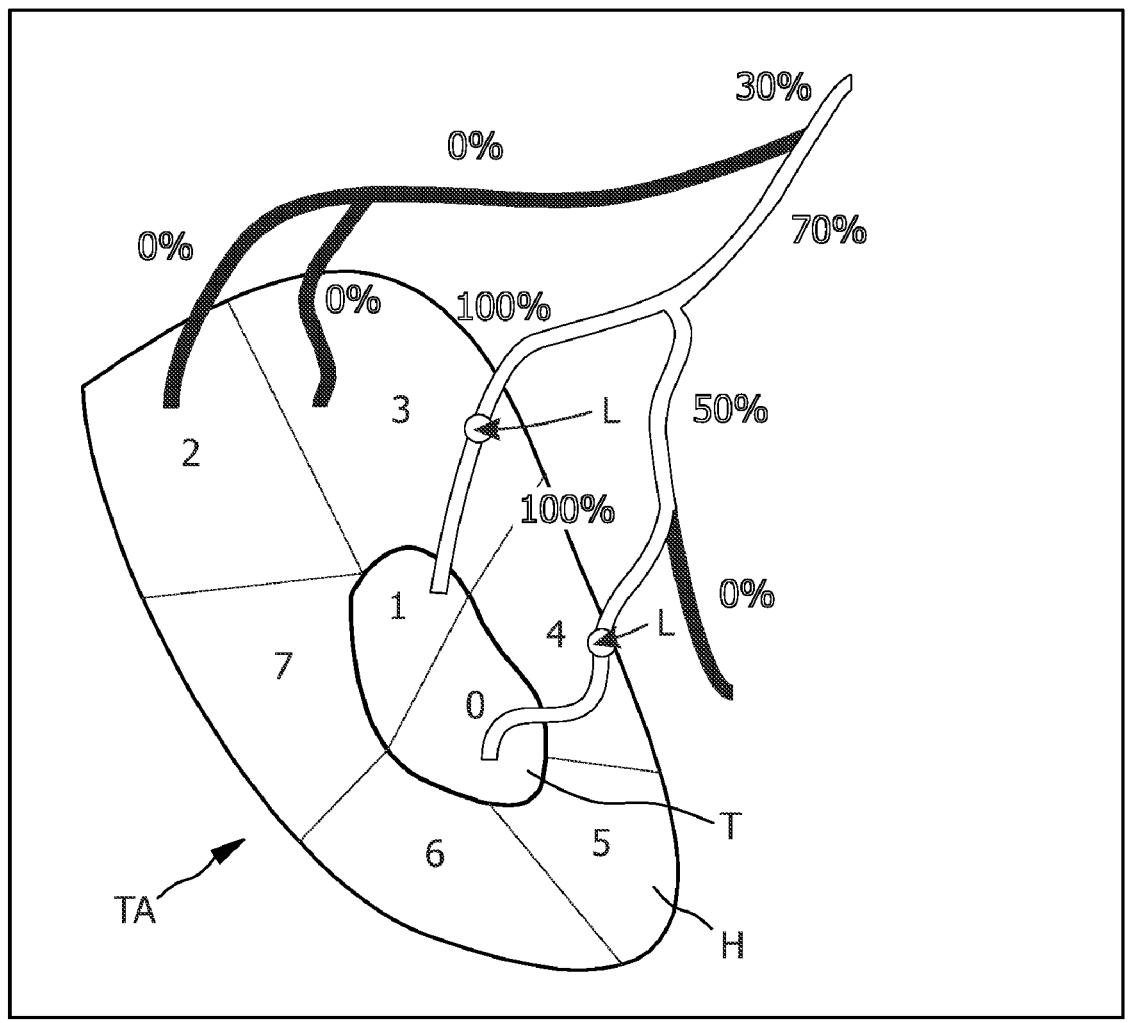

The invention will now be explained in more detail with reference to the drawings in which FIG. 1 shows a block diagram of an apparatus according to the invention, FIG. 2 shows an illustration of the topology of a segmented vessel tree, FIG. 3 shows an illustration of the measurement of the volume flow rates in the end segments of the vessel tree, FIG. 4 shows a back propagation of weighted volume flow rates to potential drug injection points, FIG. 5 shows the efficiency of a drug injection into the respective vessel segments, and FIG. 6 shows a roadmap to the optimal location of targeted drug delivery.

An embodiment of the apparatus according to the present invention for X-ray supported assessment of potential locations for targeted drug delivery is schematically illustrated in the block diagram of FIG. 1. Before the optimal injection point for injection of the drug into patient's body 1 can be determined, image data of the patient 1 need to be acquired by image data acquisition means 2, such as an X-ray device for 3D rotational angiography (3DRA) or other medical diagnostic imaging means like CT, MR or an ultrasound device. The obtained image data is generally stored in a memory 3. Of course, the subsequent processing by the data processing device 4 can be done directly after data acquisition or data storage, but it can also be done at any time later.

In order to estimate the impact of chemoembolization, during a dynamic data acquistion showing the transport of contrast agent in a vessel tree the distribution of contrast agent in the vessel tree in the target area is analysed. To this aim, the vessel tree topology is analysed first by an identification unit 41. In particular, the determination of vessel end points and bifurcations is important for the subsequent processing. Also said target, e.g. the tumor, has to be identified. In a preferred embodiment the healthy tissue is segmented into compartments fed by the same artery in addition. Such a segmented vessel topology, which can be derived from the acquired image data is shown in FIG. 2 in which a number of bifurcations $B_1$ to $B_4$ and a number of segments $S_1$ to $S_9$ are indicated. An algorithm for the analysis of the vessel tree topology in planar acquisitions like X-ray is, for instance, described in C. Kirbas and F. K. H. Quek, "A Review of Vessel Extraction Techniques and Algorithms", Vision Interfaces and Systems Laboratory (VISLab), Department of Computer Science and Engineering, Wright State University, Dayton, Ohio, November 2002. Another algorithm is described in H. Schmitt et al. "An X-ray-based method for the determination of the contrast agent propagation in 3-D vessel structures", IEEE Transactions on Medical Imaging, Vol. 21, No. 3, March 2002.

Preferably the vessel tree is segmented by threshold segmentation in a segmentation unit 411. Then the resulting 3D vessel tree is portioned into segments by region growing. Beginning from a seed point all connected voxels are detected. Then it is checked whether all voxels of this generation are connected. If this is the case all voxels belong to the same vessel segment. In case of a bifurcation of the vessel tree a generation splits up into two or more connected components. The voxels are labeled as new vessel segments. In the next step the neighbor voxels of the current generation are detected. The procedure terminates when all voxels are labeled or the remaining voxels cannot be reached by the seed point.

In another embodiment the skeleton of the binary vessel tree is calculated first. Bifurcations are voxels with more than two neighbors. Further approaches, which can also be used instead, exploit the information provided by contrast agent dynamics to increase robustness in planar acquisitions in addition. It should further be noted that the segmentation and analysis of the vessel tree topology can also be done in advance by other means and can be used on the memory 3 as well.

Since a certain compartment of an organ is basically fed by a single artery, the amount of chemoembolic material transported through the feeding artery is directly linked to the impact of chemoembolization in that particular region. Since the anatomy of the organ is well-known in advance, an automatic partitioning, preferably in combination with a manual readjustment for the individual patient, is performed in identification unit 41. In order to distinguish between desired and unwanted distribution of chemoembolic material, the compartments are divided up into healthy tissue and tumor/target region. As the tumor itself is not visible in X-ray projections, diagnostic imagery, for example CT/MR, is used to match it with the topology information to locate the target area.

Subsequently the percentage of drug material delivered to the target is determined in a flow determination unit 42. First, the volume flow rates of the end segments $S_1, S_2, S_5, S_6$ and $S_7$ of the vessel tree are measured by measurement unit 421. The volume flow rate $Q_i$ of a final vessel segment indicates how much chemoembolic material enters the associated compartment. However, the biological impact of local drug delivery depends not only of the amount of drug but also on the type of tissue. Hence, the volume flow rate is preferably weighted in a weighting unit 422 by a factor wi indicating how vulnerable the tissue is. For the measurement of volume flow rates in 2D, well-known algorithms can be applied as described in S. D. Shpilfoygel, R. A. Close, D. J. Valentino and G. R. Duckwiler, "X-ray videodensitometric methods for blood flow and velocity measurement: A critical review of literature", Med. Phys. 27(9), p. 2008-2023, 2000. Lately, preferable approaches in 3D are available and can be used as well, such as described in a European patent application EP05100798.7 (Philips docket number NL050108, "System for the determination of vessel geometry and flow characteristics") in combination with well known videodensitometric methods for blood flow measurement, e.g. bolus arrival times. FIG. 3 shows an illustration of the measurement of the volume flow rates in the end segments of the vessel tree as obtained by measurement unit 421.

An overview of well known videodensitometric methods for blood flow measurement is given in S. D. Shpilfoygel, R. A. Close, D. J. Valentino and G. R. Duckwiler, "X-ray videodensitometric methods for blood flow and velocity measurement: A critical review of literature", Med. Phys. 27(9), p. 2008-2023, 2000. Important algorithms are, e.g. bolus arrival time algorithms which determine the time at which a representative feature of the contrast agent bolus has arrived at position l. Given two such observations, the difference Δt is extracted that the bolus took to travel the distance Δl between the two fixed ROIs and is subsequently used to calculate the blood velocity and the volume flow, respectively. Of course the represented feature can also be extracted from a fitted model of the time intensity curve instead of using the time intensity curve themselves. Instead of bolus arrival time algorithms, tracking bolus edge algorithms can be used, too. Here, the position of the bolus in the DSA image is determined for the time instant. Exploiting two such observations, the distance Δl that the bolus has traveled between two fixed time instances can be extracted and again be used for the velocity calculation.

A complete different approach is the integral surface method. Here, the volume flow rate of a reservoir with a single inflow is the difference between the content of the reservoir at two different time instances divided by the time difference. An instant volume flow rate is obtained when this time difference is as small as possible. Still further, approaches which exploited the continuity equation for optical flow are known. Of course this listing of volume flow measurement algorithms is not complete and other known algorithms can be applied as well.

Subsequently, the weighted volume flow rates are projected back to the injection point of contrast agent in a back propagation unit 423. As a result (shown in FIG. 4) the weighted amount of chemoembolic material entering the tumor T (i.e. the target) or affecting the healthy tissue H of the target area TA is now known for each segment of the vessel tree. The healthy tissue can be partitioned into different compartments each fed by a certain feeding artery. The result of the segmentation is also depicted in FIG. 4 where to each compartment a specific number is assigned.

The proportion of chemoembolic material entering the tumor indicates the efficiency η of a targeted drug delivery at a certain location. Hence, the efficiency is calculated in the flow determination means 42, for instance by dividing the sum of weighted volume flow rates of tumor feeding arteries by the overall sum of weighted volume flow rates $$\eta = \frac{\sum_{\forall i \in tumor} w_i \cdot Q_i}{\sum_{\forall i \in tumor} w_i \cdot Q_i + \sum_{\forall i \in healthy\ tissue} w_i \cdot Q_i}. \quad (1)$$

On the other hand $$\mu = 1 - \eta \quad (2)$$

is an indicator for the damage caused by chemoembolization in healthy tissue. If μ is close to 0 and η is close to 1, respectively, most of the chemoembolic material will enter the tumor and the associate vessel segment is suitable as a drug injection point.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Alternatively, the efficiency can be measured differently. For example, positive weighting factors are assigned to a tumor whereas negative weighting factors are assigned to healthy tissue. Then the weighted flow rates just have to be accumulated in the backprojection procedure. Then a high and positive result for a particular branch indicates a good injection point whereas negative results mark inappropriate injection points.

Since all segments of the vessel tree are potential drug injection points, the efficiency of a targeted drug delivery is now calculated for each segment using equation (1). The result is depicted in FIG. 5 exemplarily. The optimal location L of targeted drug delivery is selected by a selection unit 43 as the segment with the highest efficiency η. Finally, in order to support the interventionalist in the advancement of the catheter, a roadmap to the optimal drug injection point can optionally be displayed on the display 5 as shown in FIG. 6. But generally, for visualization the display of the efficiencies of each vessel branch is sufficient. Of course a verification of the efficiency of targeted drug delivery at the optimal injection point can be made in addition by a second CA acquisition and an injection of contrast material at the detected optimal injection point.

The main field of application of the proposed invention for potential drug injection points is to support the planning of targeted drug delivery during cancer treatment. Since especially chemoembolization of liver tumors is a growing application, the proposed functionality is an important extension of the application range of known tools. The new assessment of potential injection points for chemoembolic material can be added to planed perfusion and flow software packages and increases the value of angiograms for interventions.

The basic idea of the invention is to provide the interventionalist with an objective and quantitative assessment of all potential drug injection points with just a single injection of contrast agent, at least if the potential drug injection points in the vessel tree are located downstream of injection points of the injection point of the first injection. For this purpose, the percentage of injected chemoembolic material delivered to the tumor and the amount of drug effecting healthy tissue is determined for each potential injection point. In an exemplary realization, the amount of chemoembolic material entering the tumor is estimated by volume blood flow rate measurements in combination with a back propagation of weighted flow rates in 3D.

Since a more tightly focused drug delivery is provided, the quantum of falsely delivered chemoembolic material is reduced. In some previously untreatable cases targeted drug delivery can therefore become applicable because healthy tissue is harmed to a lower extent. In any case, the outcome of the intervention is improved.

As the approach also maps the evaluation of potential injection points to the 3D vessel tree, systematic guidance to the optimal location of arterial drug delivery is provided in addition.

While a single injection of contrast agent should be sufficient, several injections are possible as well. If contrast agent is injected at different locations, the efficiency results of all injections can be merged. As a result, information about branches that are not visible in one particular contrast agent injection is depicted as well. Additionally information becomes more reliable since the given efficiency for a particular branches consists of several observations. Results, which are obtained for injection points closest to the particular branch, are more reliable than others and should thus influence the evaluation of the potential injection points stronger.

This can be done by an automatic assignment of a measure of uncertainty to each videodensitometric measurement. This measure can then be used to weight the different observations where to the more reliable results a stronger weighting factor is assigned. This weighting step could, for instance, also be done by the weighting unit 422 in addition or alternatively to the above described weighting.

The invention claimed is:

1. Apparatus for determining an injection point for targeted drug delivery into a patient's body by injection of the drug into a vessel feeding a target area including a target comprising:
    a processor programmed to:
        identify a vessel tree of vessels feeding said target area,
        determine a percentage of a drug material which would be delivered to said target via branches of the vessel tree after injection into each of a plurality of different potential injection points in the branches of said vessel tree,
        select as an optimal injection point a one of the plurality of different potential injection points which results in a highest percentage of drug delivery to said target; and
    a display device which displays the selected one of the potential injection points.

2. The apparatus as claimed in claim 1, wherein determining the percentage of the drug material delivered to the target includes:
    measuring the volume flow rates of end segments of the vessel tree after injection of a contrast agent into a feeding vessel of said vessel tree, said volume flow rates indicating how much drug material enters the target area through said end segments for each of the plurality of different potential injection points.

3. The apparatus as claimed in claim 2, wherein determining the percentage of the drug material delivered to the target includes:
    backprojecting said volume flow rates to the plurality of different potential injection points in said vessel tree.

4. The apparatus as claimed in claim 2, wherein determining the percentage of the drug material delivered to the target includes:
    determining said percentages of drug delivery by determining a criterion to be used for evaluation of potential injection points, said criterion being determined by dividing a sum of volume flow rates of target feeding vessels by an overall sum of volume flow rates.

5. The apparatus as claimed in claim 2, wherein determining the percentage of the drug material delivered to the target includes:
    weighting said volume flow rates by uncertainty factors, indicating how uncertain a measured volume flow rate is.

6. The apparatus as claimed in claim 2, wherein determining the percentage of the drug material delivered to the target includes:
    weighting said volume flow rates by weighting factors, indicating to what extent the drug harms the tissue located at the end of the respective end segment of the vessel tree.

7. The apparatus as claimed in claim 6, wherein determining the percentage of the drug material delivered to the target includes:
    backprojecting the weighted volume flow rates to the plurality of different potential injection points in the branches of the vessel tree.

8. The apparatus as claimed in claim 6, wherein determining the percentage of the drug material delivered to the target includes:
    determining the percentages of drug material delivery based on a criterion in which a sum of the weighted volume flow rates of the target feeding vessels is divided by an overall sum of volume flow rates.

9. The apparatus as claimed in claim 1, wherein identifying the vessel tree includes:
    distinguishing healthy tissue from the target in the target area and for distinguishing first end segments of said vessel tree feeding healthy tissue from second end segments of said vessel tree feeding the target.

10. The apparatus as claimed in claim 9,
    wherein determining the percentage of the drug material delivered to the target includes determining the percentage of drug material delivered to said target and surrounding healthy tissue in the target area after injection into different potential injection points in said vessel tree upstream from the target and the surrounding healthy tissue, and
    wherein selecting the optimal injection point includes selecting the one of the potential injection points which results in a highest percentage of drug delivery to said target and a lowest damage to healthy tissue.

11. The apparatus as claimed in claim 1, wherein identifying the vessel tree includes:
    segmenting said target or said target area into compartments of healthy tissue and target material, said compartments being fed by different end segments of said vessel tree.

12. The apparatus as claimed in claim 1, wherein identifying the vessel tree includes:
    partitioning said target area into compartments fed by a feeding artery of said vessel tree.

13. The apparatus as claimed in claim 1, wherein the display device displays the vessel tree.

14. The apparatus as claimed in claim 13, wherein said display device further displays with said vessel tree at least one of percentages of drug delivery for different segments of said vessel tree and results of an evaluation.

15. A method for determining an injection point for targeted drug delivery into a patient's body by injection of the drug into a vessel feeding a target area including a target comprising the steps of:

with a processor, identifying in an acquired diagnostic image a vessel tree with branch vessels feeding said target area, with the processor, determining the percentage of drug material delivered to said target via branch vessels of the vessel tree after injection into each of a plurality of different potential injection points in the branch vessels of said vessel tree, with the processor, selecting a one of the plurality of potential injection points in the branch vessels which results in a highest percentage of drug delivery to said target, with a display device, displaying the selected one of the potential injection points.

16. The method as claimed in claim 15, wherein the vessel tree includes branching blood vessels which define a plurality of segments, the method further including:

measuring volume flow rates in the segments of the vessel tree.

17. The method as claimed in claim 15, wherein the vessel tree feeds both the target and healthy tissue, the method further including:

for each of the potential injection points, determining a portion of the drug delivered to the healthy tissue.

18. A non-transitory computer readable medium carrying program code which when executed by a computer causes the computer to perform the steps as claimed in claim 15.

19. An apparatus for determining an injection point into a blood vessel for a drug which targets a cancer and harms healthy tissue, the apparatus comprising:

a processor programmed to:

segment a diagnostic image to generate a vessel tree depicting blood vessels which branch to define a plurality of branch segments, some of the branch segments feeding the cancer and some feeding the healthy tissue, determine relative flow rates in the branch segments, determine from the relative flow rates an injection point in one of the branch segments upstream from the cancer which maximizes delivery of the drug via the selected branch segment to the cancer and minimizes harm to the healthy tissue; and a display device which displays the vessel tree and an indication of the determined injection point.

* * * * *